US005798396A

United States Patent [19]

Takahashi et al.

[11] Patent Number: 5,798,396

[45] Date of Patent: Aug. 25, 1998

[54] SULFONIUM SALT-CONTAINING COMPOUNDS AND INITIATORS OF POLYMERIZATION

[75] Inventors: Eiji Takahashi; Hiroo Muramoto, both of Ichihara, Japan

[73] Assignee: Nippon Soda Co., Ltd., Tokyo, Japan

[21] Appl. No.: 704,631

[22] PCT Filed: Mar. 7, 1995

[86] PCT No.: PCT/JP95/00364

§ 371 Date: Sep. 4, 1996

§ 102(e) Date: Sep. 4, 1996

[87] PCT Pub. No.: WO95/24387

PCT Pub. Date: Sep. 14, 1995

[30] Foreign Application Priority Data

Mar. 9, 1994 [JP] Japan .................................... 6-065719

[51] Int. Cl.[6] ................................ C08F 2/50; C08F 4/00; C07C 381/12

[52] U.S. Cl. ................................ 522/15; 522/25; 522/31; 522/170; 522/181; 522/188; 522/167; 526/222; 528/90; 528/408; 528/410; 568/18; 568/39; 568/42; 568/43; 568/53; 568/54; 568/55; 568/56; 568/74; 568/75; 568/77

[58] Field of Search ................................ 522/31, 15, 25, 522/170, 167, 181, 188; 526/222; 528/90, 408, 410; 568/18, 39, 42, 43, 53, 54, 55, 56, 74, 75, 77

[56] References Cited

U.S. PATENT DOCUMENTS

| | | | |
|---|---|---|---|
| 3,133,971 | 5/1964 | MacGregor | 260/607 |
| 5,159,088 | 10/1992 | Schwalm | 522/31 |
| 5,399,596 | 3/1995 | Kouge et al. | 522/31 |
| 5,648,196 | 7/1997 | Frechet et al. | 522/31 |

FOREIGN PATENT DOCUMENTS

| | | | |
|---|---|---|---|
| 39-24884 | 11/1964 | Japan . | |
| 2-1470 | 1/1990 | Japan . | |
| 2-250836 | 10/1990 | Japan . | |
| 40-3059001 | 3/1991 | Japan | 522/31 |
| 3-200761 | 9/1991 | Japan . | |

OTHER PUBLICATIONS

Japan. kOKAI No. 58-37003, P.T.O. translation, Mar. 4, 1983.

*Primary Examiner*—Susan W. Berman

*Attorney, Agent, or Firm*—Jacobson, Price, Holman & Stern, PLLC

[57] ABSTRACT

The present invention is directed to sulfonium salt-containing compounds represented by a following general formula;

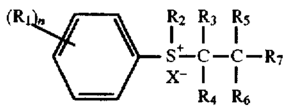

(I)

wherein $R_1$ is alkyl containing from 1 to 18 carbon atoms, hydroxy, alkoxy containing from 1 to 18 carbon atoms, alkylcarbonyloxy containing from 1 to 18 carbon atoms or halogen, n is any of 0, 1, 2 or 3, however, each of $R_1$ may be different from the others when n is 2 or more, $R_2$ is alkyl containing from 1 to 6 carbon atoms, $R_3$ and $R_4$ are each independently hydrogen or alkyl containing from 1 to 6 carbon atoms, $R_5$ and $R_6$ are each independently hydrogen, alkyl containing from 1 to 6 carbon atoms, hydroxy, alkoxy containing from 1 to 6 carbon atoms, alkylcarbonyloxy containing from 1 to 18 carbon atoms or aromatic carbonyloxy, and $R_7$ is alkyl containing from 4 to 20 carbon atoms or a group represented by a following formula;

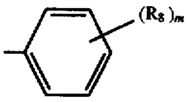

wherein $R_8$ is alkyl containing from 1 to 18 carbon atoms, hydroxy, alkoxy containing from 1 to 18 carbon atoms, alkylcarbonyloxy containing from 1 to 18 carbon atoms, aromatic carbonyloxy or halogen, m is any of 0, 1, 2 or 3, however, each of $R_8$ may be different from the others if m is 2 or more, and X is non-nucleophilic anion residue, and hardening compositions comprising said sulfonium salt-containing compounds.

In particular, a hardening composition comprising the sulfonium salt-containing compound represented by the general formula [I] shown above, a sensitizer and a cationic polymerizable compound can harden in a short time under either heating or irradiation of light or the like, and therefore, said hardening composition can be suitably used for coating materials, adhesives, photoresists, etc.

16 Claims, No Drawings

SULFONIUM SALT-CONTAINING COMPOUNDS AND INITIATORS OF POLYMERIZATION

FIELD OF THE INVENTION

The present invention is related to novel sulfonium salt-containing compounds and hardening compositions comprising said compounds, and more particularly to cationic hardening compositions of which film with a thickness ranging from very thin to thick can harden in a short time under heating or irradiation of active energy ray, such as light, electronic ray and X-ray. The hardened-products of said cationic hardening compositions have excellent physical properties, and therefore, those can be used for coating materials, adhesives, photoresists, etc.

BACKGROUND ART

The sulfonium salt-containing compounds similar to the ones specified in the present invention are described in Japanese Patent Laid-Opened No. Sho 50-151997, No. Sho 50-158680 and No. Hei 2-178303, respectively, wherein it is disclosed that the sulfonium salt-containing compounds can be used as a catalyst for hardening of cationic polymerizable compounds, such as epoxy compounds, under the application of radiation, such as light, electronic ray and X-ray.

However, the sulfonium salt-containing compounds described in the Japanese Patent Laid-opened No. Sho 50-151997 is effective for photo-setting, but said compounds have problems such that those can be hardly used for the hardening of thick films due to almost no-effectiveness as a catalyst for thermo-setting, expensive production cost owing to complicated synthesizing processes, and low solubility to monomers. Also, the compounds disclosed in the Japanese Patent Laid-Opened No. Hei 2-178303 can harden thick films since those can work as a catalyst for thermo-setting, however, those have very poor activity as a catalyst for photo-setting and have less solubility to monomers. Again, aliphatic compounds containing sulfonium salt reported by Endo et al. (IUPAC MACRO 88 PREPR. 90 (1988)) can work as a catalyst for thermo-setting and are capable of hardening thick films, however, those activity as a catalyst for photo-setting is very poor.

DISCLOSURE OF THE INVENTION

It is an object of the present invention to provide sulfonium salt-containing compounds which have high sensitivity to either heat or irradiation of active energy ray, such as light, electronic ray and X-ray, as well as to provide cationic hardening compounds, of which film with a thickness ranging from very thin to thick can harden in a short time and the hardened-product thereof shows to have excellent physical properties.

The inventors of the present invention made various examinations for aiming at accomplishing the object described above, then found that a hardening composition comprising sulfonium salt-containing compound, sensitizer and cationic polymerizable compound, of which film with a thickness ranging from very thin to thick can harden when it is subjected to either heating or irradiation of active energy ray, such as light, electronic ray and X-ray and the hardened product thereof has excellent physical properties, thereby completed the present invention.

The present invention is directed to sulfonium salt-containing compounds as represented by a following general formula (I);

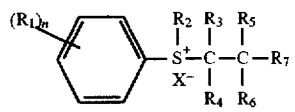

wherein $R_1$ is alkyl containing from 1 to 18 carbon atoms, hydroxy, alkoxy containing from 1 to 18 carbon atoms, alkylcarbonyl containing from 1 to 18 carbon atoms or halogen, n is any of 0, 1, 2 or 3, however, R may be different from the groups above when n is 2 or more, $R_2$ is alkyl containing from 1 to 6 carbon atoms, $R_3$ and $R_4$ are each independently hydrogen or alkyl containing from 1 to 6 carbon atoms, $R_5$ and $R_6$ are each independently hydrogen, alkyl containing from 1 to 6 carbon atoms, hydroxy, alkoxy containing from 1 to 6 carbon atoms, alkylcarbonyl containing from 1 to 18 carbon atoms or aromatic carbonyl, $R_7$ is alkyl containing from 4 to 20 carbon atoms or a group represented by a following formula;

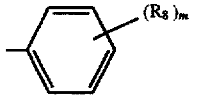

wherein $R_8$ is alkyl containing from 1 to 18 carbon atoms, hydroxy, alkoxy containing from 1 to 18 carbon atoms, alkylcarbonyl containing from 1 to 18 carbon atoms, aromatic carbonyl or halogen, m is any of 0, 1, 2 or 3, however, $R_8$ may be different from the groups above when m is 2 or more, and X is non-nucleophilic anion residue, and hardening compositions comprising said sulfonium salt-containing compound, sensitizer and cationic polymerizable compound.

In the general formula (I) shown above, alkyl, such as methyl, ethyl, propyl, isopropyl, butyl, isobutyl, tert-butyl, decyl and dodecyl, halogen, such as fluorine, chlorine, bromine and iodine, hydroxy, alkoxy, such as methoxy, ethoxy, propoxy, butoxy, hexyloxy, decyloxy and dodecyloxy, and alkylcarbonyl, such as acetoxy, propionyloxy, decylcarbonyloxy and dodecylcarbonyloxy, can be exemplified as the substituent for phenyl represented by $R_1$ and $R_8$. For the examples of alkyl containing from 1 to 6 carbon atoms represented by $R_2$, methyl, ethyl, propyl, isopropyl, butyl, isobutyl, tert-butyl, amyl, hexyl and the like can be exemplified. As alkyl, alkoxy and alkyl contained in the alkylcarbonyl represented by $R_3$, $R_4$, $R_5$ and $R_6$, respectively, the groups as recited in the above examples can be exemplified, and the example of aromatic carbonyl for $R_6$, benzoyloxy and the like can be exemplified. For the example of alkyl for $R_7$, $C_4$-alkyl, $C_6$-alkyl, $C_{10}$-alkyl, $C_{16}$-alkyl and the like can be exemplified. For the examples of non-nucleophilic anion residue represented by X, $SbF_6$, $AsF_6$, $PF_6$, $BF_4$ and the like can be exemplified.

The representative examples for the sulfonium salt-containing compounds of the present invention are shown in form of structural formulas hereinbelow. In these formulas, X represents non-nucleophilic anion residue, such as $SbF_6$, $AsF_6$, $PF_6$, $BF_4$ and the like.

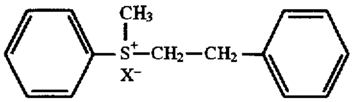

-continued
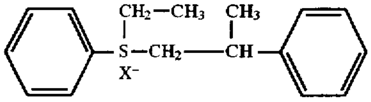
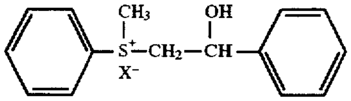
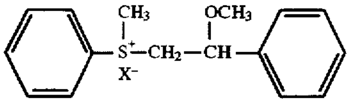
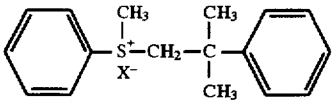
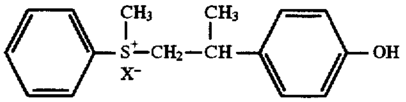
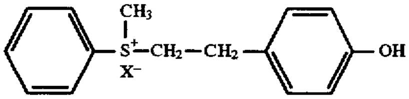
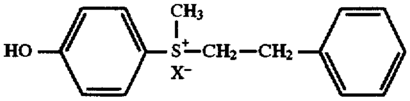
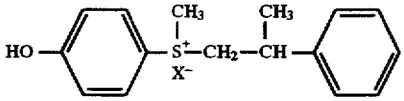
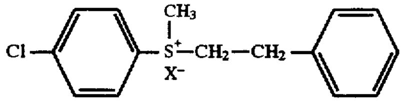
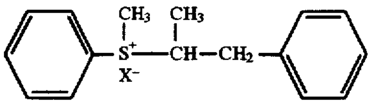
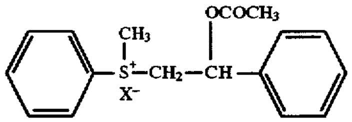
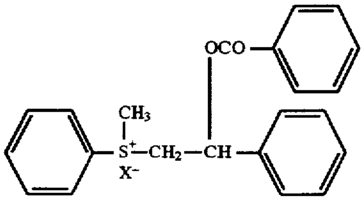
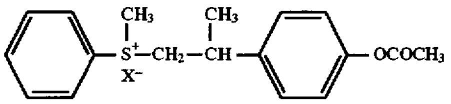
-continued
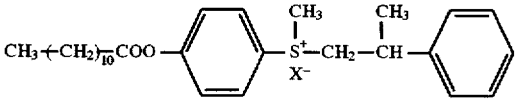
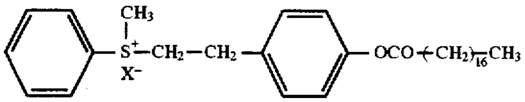
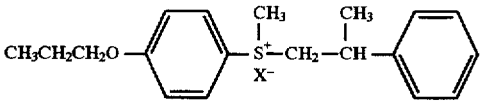
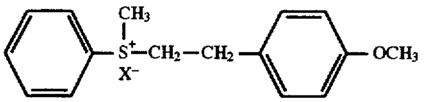
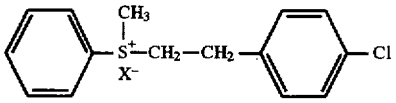
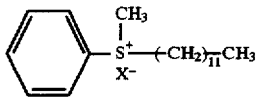
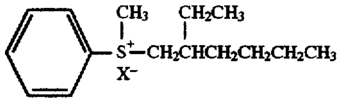
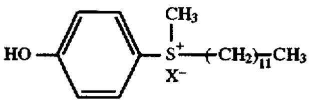
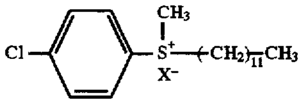
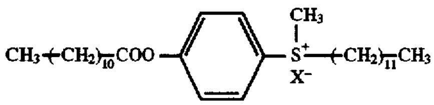
The sulfonium salt-containing compounds of the present invention can be manufactured according to the following reaction scheme;
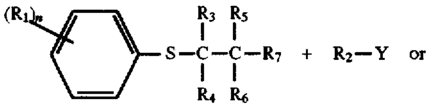
(II) (III)
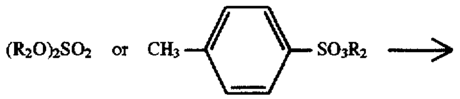
(IV) (V)

-continued

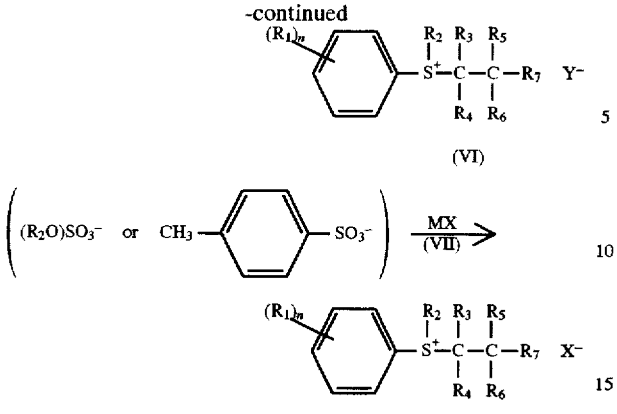

(VI)

(I)

wherein Y represents halogen and M represents alkaline metal.

The reaction of a compound represented by a general formula [II] with any of compounds represented by general formulas [III], [IV] or [V] is carried out for 1 to dozens of hours at a temperature from room temperature to 150° C., preferably from 30° to 80° C., in an organic solvent if required. After the completion of the reaction, the solution reacted is added with water and compound represented by a general formula [VII], then stirred. Compound precipitated is either taken out by filtration or extracted with an organic solvent to obtain the objective compound.

The sulfonium salt-containing compounds of the present invention can harden cationic polymerizable compounds not only under heating but also under irradiation of active energy ray, such as light, electronic ray and X-ray. However, by using a sensitizer jointly, the sulfonium salt-containing compounds of the present invention can harden cationic polymerizable compounds in a shorter time than the case without using a sensitizer.

The sensitizer used in the present invention is defined as compounds capable of accelerating photo-reaction of the sulfonium salt-containing compounds. For the examples of such sensitizer, compounds easily discharging hydrogen radicals, stop agents for radical polymerization, compounds capable of reacting with a sulfonium salt-containing compound then consequentially discharging protons during a process of photo-reaction of the sulfonium salt-containing compound, electron donors, etc. can be exemplified. More particularly, compounds, such as thiol compounds and hydrocarbons, which easily discharge hydrogen radicals, stop agent for radical polymerization, such as 4-methoxy phenol, and 4-benzyloxy phenol, 4-methoxy-2-(tert-butyl) phenol, hydroquinone and phenothiazine, 4-methoxy-1-naphthol, 2-hydroxy dibenzofuran, 9, 10-dimethoxy anthracene, N, N-diphenyl-p-phenylenediamine, compounds represented by the following chemical formula;

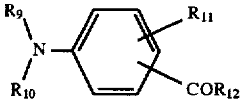

(VIII)

wherein $R_9$ and $R_{10}$ can be identical or different alkyl containing from 1 to 20 carbon atoms formed in either straight or branched chain, and $R_9$ and $R_{10}$ may bound with each other in an unit, $R_{11}$ is hydrogen, lower alkyl or halogen, $R_{12}$ is hydrogen, hydroxy, unsubstituted or substituted alkyl, phenyl optionally having substituent, benzyl optionally having substituent, unsubstituted or substituted alkoxy, unsubstituted or substituted phenoxy, or benzyloxy optionally having substituent, and the like, can be used as the sensitizer. However, phenol derivatives, such as 4-methoxy phenol, is preferably used.

For the examples of the compounds represented by the general formula [VIII] shown above, p-dimehtylamino benzoic acid, p-dimethylamino benzaldehyde, p-dimethylamino ethyl benzoate, 2-n-butoxyethyl-p-dimethylamino benzoate, p-dimethylamino isoamyl benzoate, p-dimethylamino acetophenone, p-diethylamino benzoic acid, p-diethylamino benzaldehyde and the like can be exemplified.

For the examples of the cationic polymerizable compounds used in the present invention, the following compounds can be exemplified. (a) Vinyl compounds:

Styrenes including styrene, α-methyl styrene, p-methoxy styrene, p-tert-butoxy styrene and the like; alkyl vinyl ethers including methyl vinyl ether, n-butyl vinyl ether, ethyl vinyl ether, isobutyl vinyl ether, cyclohexyl vinyl ether, 2-chloroethyl vinyl ether, 2-phenoxyethyl vinyl ether, 2-hydroxyethyl vinyl ether, 4-hydroxybutyl vinyl ether, stearyl vinyl ether, 2-acetoxyethyl vinyl ether and the like; alkenyl vinyl ethers including allyl vinyl ether, 2-methacryloyloxyethyl vinyl ether, 2-acryloyloxyethyl vinyl ether and the like; aryl vinyl ethers including phenyl vinyl ether, p-methoxyphenyl vinyl ether and the like; cationic polymerizable nitrogen-containing compounds including N-vinyl carbazole, N-vinyl pyrrolidone and the like; and multifunctional vinyl compounds including butanediole divinyl ether, triethylene glycol divinyl ether, cyclohexanediole divinyl ether, 1,4-benzene dimethanol divinyl ether, hydroquinone divinyl ether, resolcinole divinyl ether and the like. (b) Epoxy compounds:

Monofunctional monomers including phenyl glycidyl ether, p-tert-butylphenyl glycidyl ether, butyl glycidyl ether, 2-ethylhexyl glycidyl ether, allyl glycidyl ether, 1,2-butylene oxide, 1,3-butadiene monooxide, 1,2-dodecylene oxide, epichlorohydrin, 1,2-epoxy decane, ethylene oxide, propylene oxide, styrene oxide, cyclohexene oxide, 3-metacryloyloxymethyl cyclohexene oxide, 3-acryloyloxymethyl cyclohexene oxide, 3-vinyl cyclohexene oxide, 4-vinyl cyclohexene oxide and the like; and multifunctional epoxy compounds including 1, 1,3-tetradecadiene dioxide, limonene dioxide, 3,4-epoxycyclohexylmethyl-(3,4-epoxycyclohexyl)carboxylate, di-(3,4-epoxycyclohexyl)adipate, phenyl glycidyl ether, bisphenol A epoxy resin, bisphenol F epoxy resin, bisphenol S epoxy resin, halogenated bisphenol A epoxy resin, o-, m- and p-cresol epoxy-novolak resins, halogenated o-, m- and p-cresol epoxy-novolak resins, phenol epoxy-novolak resin, polyglycidyl ether of polyhydric alcohol and the like. (c) Bicyclo-orthoesters including 1-phenyl-4-ethyl-2,6,7-trioxabicyclo[2.2.2]octane, 1-ethyl-4-hydroxymethyl-2,6,7-trioxabicyclo[2.2.2]octane and the like. (d) Spiro-orthocarbonates including 1,5,7,11-tetraoxaspiro[5.5] undecane, 3,9-dibenzyl-1, 5, 7, 11-tetraoxaspiro[5, 5]undecane, 1, 4, 6-trioxaspiro[4, 4]nonane, 2-methyl-1,4, 6-trioxaspiro[4,4]nonane, 1,4,6-trioxaspiro[4,5]decane and the like.

The compounds recited above can be used either alone or in combination of more than two compounds.

In the present invention, the compounding ratio of the sulfonium salt-containing compound to the cationic polymerizable compound is from 0.01 to 20 parts, and preferably from 0.1 to 10 parts, respective to 100 parts of the cationic polymerizable compound. If the compounding ratio of the sulfonium salt-containing compound is less than the above range, hardening property of the cationic polymerizable compound deteriorates, while the property of hardened-product deteriorate if the compounding rate exceeds the above range.

On the other hand, the compounding ratio of the sensitizer to the cationic polymerizable compound is from 0.001 to 10 parts, and preferably from 0.01 to 5 parts, respective to 100 parts of the cationic polymerizable compound. If said compounding ratio of the sensitizer is less than the above range, photo-reactivity of the sulfonium salt-containing compound deteriorates, while the property of the hardening composition deteriorate if the compounding rate exceeds the above range.

The hardening compositions of the present invention can easily harden under light.

For hardening, light having a wave length being less than 500 nm, and most preferably ultraviolet ray, is found to be effective. Therefore, low pressure mercury lamp, medium pressure mercury lamp, high pressure mercury lamp, extra-high pressure mercury lamp, metal halide lamp, Xenon discharge lamp, carbon arc lamp and the similar can be used as a light source. Also, it is possible to use laser light as a light source.

The hardening compositions of the present invention can easily harden under irradiation of ionizing radiation, such as α-ray, β-ray, γ-ray, neutron beam, X-ray, and accelerating electronic ray. For the hardening, ionizing radiation at a dose of from 0.5 to 60M rad, and preferably from 1 to 50M rad, can normally be applied to the composition.

Also, the hardening composition of the present invention can easily harden under heating. The heating is carried out at a temperature of from 50° to 200° C., and preferably from 80° to 180° C. In addition, it is also possible to harden the composition by applying in any combination of light, ionizing radiation and heating.

BEST MODE FOR CARRYING OUT THE INVENTION

Now, the present invention is further described in detail with referring to Examples hereinbelow.

EXAMPLE 1

Synthesis of phenyldodecylmethyl sulfonium hexafluoroantimonate (Compound No. 1)

27.75 g of phenyldodecyl sulfide and 13.24 g of dimethyl sufuric acid are mixed and are allowed to stand in reaction for an hour at 80° C. and then for 2 days at 50° C. The product reacted was then dissolved into 200 g of distillated water, added with 27.48 g of potassium hexafluoroantimonate, then stirred vigorously. The product precipitated was separated and dried at 40° C. under reduced pressure. Yield: 90%.

IR spectrum data for the product obtained was as follows. IR(KBr, $cm^{-1}$): 2921, 2852, 1469, 1450, 1425, 768, 685, 655

EXAMPLE 2

Synthesis of phenyl(2-phenylethyl)methyl sulfonium hexafluoroantimonate (Compound No. 7)

42.86 g of phenyl-2-phenylethyl sulfide and 26.49 g of dimethyl sufuric acid are mixed and are allowed to stand in reaction for 3 days at 50° C. The product reacted was then dissolved into 300 g of distillated water, added with 54.97 g of potassium hexafluoroantimonate, then stirred vigorously. The product precipitated was separated and dried at 40° C. under reduced pressure. Yield: 94%.

IR spectrum data for the product obtained was as follows. IR(KBr, $cm^{-1}$): 3033, 1604, 1585, 1499, 1450, 1422, 751, 686, 659

The representative examples of the sulfonium salt-containing compounds of the present invention manufactured according to the method similar to the above are shown in Table 1, including the compounds obtained in Examples 1 and 2.

TESTS ON PHOTO-SETTING ACTIVITY

To ERL-4221 (alicyclic epoxy compound manufactured by UCC), was added 4-methoxy phenol as the sensitizer and sulfonium salt-containing compound, both dissolved in propylene carbonate, at a rate of 0.5 parts as purified for the former and at a rate of either 1.0 part when counter ion being $SbF_6^-$ or 3.0 parts when counter ion being $PF_6^-$, as purified for the later, respective to 100 parts of propylene carbonate, thereby preparing a compounded-composition. The compounded-composition was then coated to a tin plate in a thickness of 3 μm, then was subjected to hardening under light in the following condition. The composition which resulted in hardening or became tack-free was represented by a mark ○, while composition which remained tack or did not harden was represented by a mark X. The result is shown in Table 2.

Apparatus for UV Irradiation: Belt conveyor-type UV Irradiating Apparatus Lamp: 2 Kw(80w/cm) Parallel lighting type high pressure mercury lamp Distance for Irradiation: 15 cm Conveyor Speed: 10 m/min.

TESTS ON THERMO-SETTING ACTIVITY 0.5 g of the compounded-composition described above was weighed and placed in a glass sample container, then allowed to stand in a oven maintained at 150° C. for 30 minutes. The composition resulted in hardening was represented by a mark ○, and the composition which did not harden was represented by a mark X. The result is shown in Table 2.

TESTS ON STORAGE STABILITY 100 g of the compounded-composition described above was weighed and placed in a glass sample container, then allowed to stand in a oven maintained at 25° C. for one month. The composition of which viscosity having changed not more than 2 times of the original value was represented by a mark ○, and the composition of which viscosity having changed to more than 2 times of the original or the composition hardened was represented by a mark X. The result is shown in Table 2.

TABLE 1

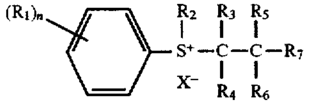

| Compound No. | Structral Formula $(R_1)_n$ | $R_2$ | $R_3$ | $R_4$ | $R_5$ | $R_6$ | $R_7$ | X | Physical Data IR ($cm^{-1}$) |
|---|---|---|---|---|---|---|---|---|---|
| 1 | - (n = 0) | $CH_3$ | H | H | H | H | $-(CH_2)_9-CH_3$ | $SbF_6$ | 2921, 2852, 1469, 1450, 1425, 785, 685, 655 |
| 2 | — | $CH_3$ | H | H | H | H | $-(CH_2)_9-CH_3$ | $PF_6$ | 2926, 2855, 1467, 1450, 1425, 844, 752, 687, 559 |
| 3 | 4-OH | $CH_3$ | H | H | H | H | $-(CH_2)_9-CH_3$ | $SbF_6$ | 3480, 2927, 2856, 1587, 1503, 1290, 838, 662 |
| 4 | 4-Cl | $CH_3$ | H | H | H | H | $-(CH_2)_9-CH_3$ | $SbF_6$ | 2927, 2855, 1577, 1482, 1098, 827, 660 |
| 5 | 4-Cl | $CH_3$ | H | H | H | H | $-(CH_2)_9-CH_3$ | $PF_6$ | 2927, 2855, 1577, 1483, 1098, 839, 559 |
| 6 | $4-CH_3-(CH_2)_{10}-COO-$ | $CH_3$ | H | H | H | H | $-(CH_2)_9-CH_3$ | $SbF_6$ | 2925, 2854, 1758, 1587, 1467, 1215, 1172, 661 |
| 7 | — | $CH_3$ | H | H | H | H | 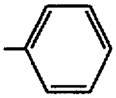 | $SbF_6$ | 3033, 1604, 1585, 1499, 1450, 1422, 751, 686, 659 |
| 8 | — | $CH_3$ | H | H | H | H | 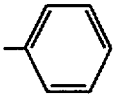 | $PF_6$ | 3035, 1604, 1500, 1450, 1425, 837, 750, 686, 558 |
| 9 | — | $CH_3$ | H | H | $CH_3$ | H | 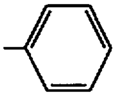 | $SbF_6$ | 2975, 1496, 1450, 1421, 753, 705, 686, 659 |
| 10 | — | $CH_3$ | H | H | $CH_3$ | H | 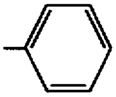 | $PF_6$ | 2976, 1496, 1450, 1422, 835, 753, 705, 686, 558 |
| 11 | — | $CH_3$ | H | H | $CH_3$ | $CH_3$ | 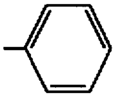 | $SbF_6$ | 2977, 1449, 989, 752, 707, 685, 659 |
| 12 | — | $CH_3$ | H | H | $CH_3$ | $CH_3$ | 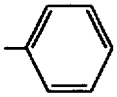 | $PF_6$ | 2981, 1449, 983, 838, 759, 711, 688, 558 |
| 13 | 4-Cl | $CH_3$ | H | H | H | H | 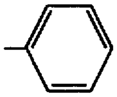 | $SbF_6$ | 3033, 1577, 1482, 1098, 827, 751, 703, 659 |
| 14 | 4-Cl | $CH_3$ | H | H | H | H | 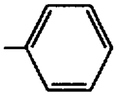 | $PF_6$ | 3030, 1577, 1482, 1098, 840, 751, 703, 558 |
| 15 | 4-OH | $CH_3$ | H | H | H | H | 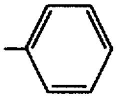 | $SbF_6$ | 3485, 1586, 1502, 1288, 838, 760, 704, 661 |
| 16 | 4-OH | $CH_3$ | H | H | $CH_3$ | H | 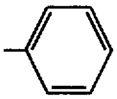 | $SbF_6$ | 3483, 1586, 1502, 1290, 837, 767, 705, 661 |
| 17 | 4-Cl | $CH_3$ | H | H | $CH_3$ | H | 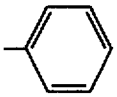 | $SbF_6$ | 3033, 1578, 1481, 1098, 826, 705, 660 |

TABLE 1-continued

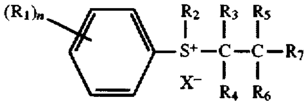

| Compound No. | Structral Formula $(R_1)_n$ | $R_2$ | $R_3$ | $R_4$ | $R_5$ | $R_6$ | $R_7$ | X | Physical Data IR ($cm^{-1}$) |
|---|---|---|---|---|---|---|---|---|---|
| 18 | 4-Cl | $CH_3$ | H | H | $CH_3$ | H | 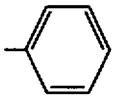 | $PF_6$ | 3034, 1578, 1482, 1098, 839, 704, 558 |
| 19 | — | $CH_3$ | H | H | H | H | 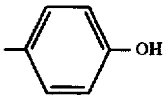 | $SbF_6$ | 3528, 1614, 1517, 1449, 1266, 835, 751, 660 |
| 20 | — | $CH_3$ | H | H | $CH_3$ | H | 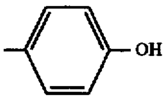 | $SbF_6$ | 3525, 1614, 1518, 1449, 1266, 837, 752, 661 |
| 21 | — | $CH_3$ | H | H | OH | H | 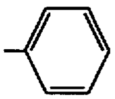 | $SbF_6$ | 3557, 3035, 1450, 1422, 1105, 752, 704, 686, 661 |
| 22 | — | $CH_3$ | H | H | $OCH_3$ | H | 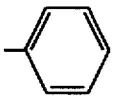 | $SbF_6$ | 3035, 1450, 1524, 1106, 753, 705, 686, 660 |

TABLE 2

| No. | Photo-Setting Capability | Thermo-Setting Capability | Storage Stability |
|---|---|---|---|
| 1 | ○ | ○ | ○ |
| 3 | ○ | ○ | ○ |
| 4 | ○ | ○ | ○ |
| 6 | ○ | ○ | ○ |
| 7 | ○ | ○ | ○ |
| 9 | ○ | ○ | ○ |
| 10 | ○ | ○ | ○ |
| 11 | ○ | ○ | ○ |
| 12 | ○ | ○ | ○ |
| 13 | ○ | ○ | ○ |
| 15 | ○ | ○ | ○ |
| 16 | ○ | ○ | ○ |
| 17 | ○ | ○ | ○ |
| 18 | ○ | ○ | ○ |
| 19 | ○ | ○ | ○ |
| 20 | ○ | ○ | ○ |
| 21 | ○ | ○ | ○ |
| 22 | ○ | ○ | ○ |
| Comparative Compound 1 | × | ○ | × |
| Comparative Compound 2 | ○ | × | ○ |

COMPARATIVE COMPOUND 1

[Compound described in IUPACMACRO 88 Prepr. 90 (1988)]

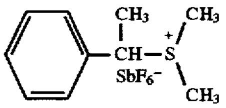

COMPARATIVE COMPOUND 2

[Compound described in JP Laid-Opened No. Sho 50-151997]

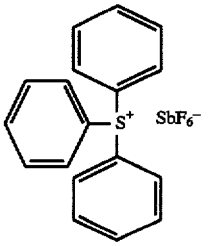

INDUSTRIAL APPLICABILITY

The sulfonium salt-containing compound of the present invention has property to show excellent reactivity under either heating or light, and it can harden films of the cationic polymerizable compound with thickness ranging from very thin to thick in a short time under either heating or irradiation of active energy ray, such as light, electronic ray and X-ray. The use of a sensitizer in combination with the sulfonium salt-containing compound can further improve photo-setting capability. Further, because of the excellent physical properties, hardened-product of said hardening composition comprising sulfonium salt-containing compound, sensitizer and cationic polymerizable compound can be used for coating materials, adhesives, photoresists, etc.

What is claimed is:

1. Sulfonium salt-containing compounds represented by a general formula (I):

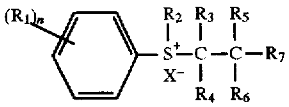 (I)

wherein $R_1$ is alkyl containing from 1 to 18 carbon atoms, hydroxy, alkoxy containing from 1 to 18 carbon atoms, alkylcarbonyloxy containing from 1 to 18 carbon atoms or halogen, n is any of 0, 1, 2 or 3, however, each of $R_1$ may be different from the others when n is 2 or more, $R_2$ is alkyl containing from 1 to 6 carbon atoms, $R_3$ and $R_4$ are each independently hydrogen or alkyl containing from 1 to 6 carbon atoms, $R_5$ and $R_6$ are each independently hydrogen, alkyl containing from 1 to 6 carbon atoms, hydroxy, alkoxy containing from 1 to 6 carbon atoms, alkylcarbonyloxy containing from 1 to 18 carbon atoms or aromatic carbonyloxy, and $R_7$ is a group represented by a following formula:

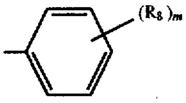

wherein $R_8$ is alkyl containing from 1 to 18 carbon atoms, hydroxy, alkoxy containing from 1 to 18 carbon atoms, alkylcarbonyloxy containing from 1 to 18 carbon atoms, aromatic carbonyloxy or halogen, m is any of 0, 1, 2 or 3, however, each of $R_8$ may be different from others if m is 2 or more, and X is non-nucleophilic anion residue.

2. An initiator of cationic polymerization comprising at least one of the sulfonium salt-containing compounds represented by the general formula (I) in claim 1.

3. A hardening composition comprising the sulfonium salt-containing compound represented by the general formula (I) in claim 4 and a cationic polymerizable compound.

4. A hardening composition comprising the sulfonium salt-containing compounds represented by the general formula (I) in claim 1, a sensitizer and a cationic polymerizable compound.

5. Sulfonium salt-containing compounds represented by a general formula (I):

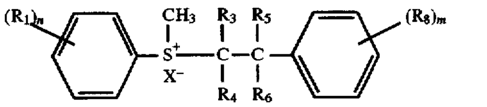 (I)

wherein $R_1$ is hydroxy, halogen or alkoxy containing from 1 to 3 carbon atoms, n is any of 0, 1, 2 or 3, however, each of $R_1$ may be different from the others when n is 2 or more, $R_3$, $R_4$, $R_5$ and $R_6$ are each independently hydrogen, methyl or methoxy, and wherein $R_8$ is methoxy or hydroxy, m is any of 0, 1, 2 or 3, however, each of $R_8$ may be different from the others if m is 2 or more, and X is non-nucleophilic anion residue.

6. An initiator of cationic polymerization comprising at least one of the sulfonium salt-containing compounds represented by the general formula (I) shown in claim 5.

7. A hardening composition comprising the sulfonium salt-containing compound represented by the general formula (I) in claim 5 and a cationic polymerizable compound.

8. A hardening composition comprising the sulfonium salt-containing compounds represented by the general formula (I) in claim 5, a sensitizer and a cationic polymerizable compound.

9. Sulfonium salt-containing compounds represented by a general formula (I):

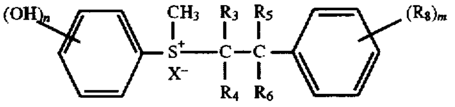 (I)

wherein n is any of 0, 1, 2 or 3

$R_3$, $R_4$, $R_5$ and $R_6$ are each independently hydrogen or methyl, and wherein $R_8$ is methoxy or hydroxy, m is any of 0, 1, 2 or 3, however, each of $R_8$ may be different from the others if m is 2 or more, and X is non-nucleophilic anion residue.

10. An initiator of cationic polymerization comprising at least one of the sulfonium salt-containing compounds represented by the general formula (I) in claim 9.

11. A hardening composition comprising the sulfonium salt-containing compound represented by the general formula (I) in claim 9 and a cationic polymerizable compound.

12. A hardening composition comprising the sulfonium salt-containing compounds represented by the general formula (I) in claim 9, a sensitizer and a cationic polymerizable compound.

13. Sulfonium salt-containing compounds represented by a general formula (I)

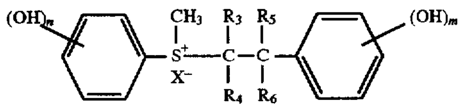 (I)

wherein n is any of 0 or 1, $R_3$, $R_4$, $R_5$ and $R_6$ are each independently hydrogen or methyl, and wherein m is any of 0 or 1, X is non-nucleophilic anion residue.

14. An initiator of cationic polymerization comprising at least one of the sulfonium salt-containing compounds represented by the general formula (I) in claim 13.

15. A hardening composition comprising the sulfonium salt-containing compound represented by the general formula (I) in claim 13 and a cationic polyermizable compound.

16. A hardening composition comprising the sulfonium salt-containing compounds represented by the general formula (I) in claim 13, a sensitizer and a cationic polyermizable compound.

* * * * *